United States Patent
Takao et al.

(10) Patent No.: US 7,588,423 B2
(45) Date of Patent: Sep. 15, 2009

(54) PUMP FOR LIQUID CHROMATOGRAPH

(75) Inventors: Kunihiko Takao, Tsuchiura (JP); Kenji Hiraku, Chiyoda (JP); Isao Hayase, Tsuchiura (JP); Hironori Kaji, Hitachinaka (JP); Masahito Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 729 days.

(21) Appl. No.: 10/695,992

(22) Filed: Oct. 30, 2003

(65) Prior Publication Data

US 2004/0164013 A1    Aug. 26, 2004

(30) Foreign Application Priority Data

Nov. 1, 2002  (JP) ............................. 2002-319222

(51) Int. Cl.
*F04B 3/00*  (2006.01)
*F04B 5/00*  (2006.01)
*F04B 25/00* (2006.01)

(52) U.S. Cl. .................. 417/254; 417/244; 417/250; 417/252

(58) Field of Classification Search ................. 417/437, 417/244, 250, 252, 254
See application file for complete search history.

(56) References Cited

U.S. PATENT DOCUMENTS

| | | | | | |
|---|---|---|---|---|---|
| 4,808,077 A | * | 2/1989 | Kan et al. | ...................... | 417/2 |
| 5,482,443 A | * | 1/1996 | Bez | .............. | 417/266 |
| 6,122,049 A | * | 9/2000 | Sugiyama et al. | ........... | 356/246 |
| 6,712,587 B2 | * | 3/2004 | Gerhardt et al. | ............. | 417/390 |

FOREIGN PATENT DOCUMENTS

| | | |
|---|---|---|
| JP | SHOU-56-169480 | 4/1994 |
| JP | HEI-06-294786 | 10/1994 |
| JP | 2000-104659 | 4/2000 |
| JP | 2004-10884 | 4/2004 |

* cited by examiner

*Primary Examiner*—Charles G Freay
*Assistant Examiner*—Patrick Hamo
(74) *Attorney, Agent, or Firm*—Mattingly & Malur, P.C.

(57) ABSTRACT

Provided is a liquid chromatograph pump system which sucks eluent from an eluent reserving container, and which feeds pressurized high pressure eluent into a column, wherein a plunger reciprocating in a cylinder is formed on its outer peripheral surface with a stepped part along the sliding direction of the plunger in the cylinder so as to define a working chamber between the stepper part and the inner wall surface of the cylinder, the flow rate of the liquid chromatograph pump being determined by the volume of the working chamber and the traveling speed of the plunger, thereby it is possible to stably feed a liquid at an extremely low flow rate, and to satisfactorily expel air bubbles upon a start of the liquid chromatograph pump system.

4 Claims, 9 Drawing Sheets

PUMP FOR LIQUID CHROMATOGRAPH

BACKGROUND OF THE INVENTION

The invention relates to a pump for liquid chromatograph, and in particular to a pump for liquid chromatograph, which is suitable for feeding liquid at a low flow rate.

In general, a conventional pump for liquid chromatograph has a plunger which reciprocates in a cylinder so as to suck and discharge eluent. In order to feed a trace of solution with a high degree of accuracy, it is required to decrease the diameter or stroke of the plunger, the smaller the solution to be fed, the more difficult the discharge of air bubbles stagnating in the inside of the pump or a solution feed passage.

For example, as disclosed in JP-A-2000-39427, there has been well-known a pump system which can feed a solution with no influence of air bubbles in the solution, and which comprises two pump units each including a first and a second pump head having different capacities, and driven by a different diameter plunger with a large diameter part and a small diameter part coaxially formed, and in which the two pump heads driven by the large diameter parts of the two different diameter plungers are used as a first pump while the two pump heads driven by the small diameter parts of the two different plungers are used as a second pump, and these first and second pumps are connected in series. Further, a heater and a gas/liquid separator are connectred to the discharge port of the first pump, and accordingly, after the air bubbles are removed from the eluent by this gas/liquid separator, the eluent is sucked into the second pump for feeding the eluent.

The above-mentioned prior art is adapted to feed a solution with a high degree of accuracy without influence of air bubbles in the solution, but there has not been sufficiently taken for this prior art such a consideration that a trace of eluent is fed with a high degree of accuracy. Further, in this prior art, the flowing velocity of eluent from the first pump which is driven by the large diameter parts of the different diameter plungers is set to be higher than that of eluent from the second pump driven by the small diameter parts of the different diameter plungers (preferably higher by two folds), and accordingly, a minimum discharge quantity of this pump system is determined by the discharge volume of the second pump. Thus, in order to set a minimum discharge volume of the pump system to a trace value, it is required to reduce the outer diameter of the second plunger which determines the discharge volume. However, it is difficult in view of machining accuracy and strength to decrease the diameter of the plunger for setting the minimum discharge quantity to a trace value.

Further, in the conventional technology, should the small diameter part of the plunger be decreased in its diameter while the large diameter thereof is unchanged so as to decrease the discharge volume of the second pump, the discharge volume of the first pump would relatively be increased. Meanwhile, even though the small diameter part of the plunger is increased in its diameter so that the discharge volume of the first pump is decreased but the discharge volume of the second pump is increased. Thus, there has been presented such a disadvantage that it is difficult to decrease the liquid feed quantity to a trace value with the use of the different diameter plunger.

Should the discharge volume of a pump be decreased so as to set the liquid feed quantity to a trace value, there would be caused such a disadvantage that a long time is required for priming a solution into several passages and the like, and for discharging air bubbles therefrom upon a start of a test.

SUMMARY OF THE INVENTION

A first object of the present invention is to provide a pump for liquid chromatography, which is suitable for setting the liquid feed quantity to a trace value.

Further, a second object of the present invention is to provide a pump system for liquid chromatograph, which can complete priming of a solution and discharge of air bubbles in a short time upon a start of a test.

In order to achieve the above-mentioned first object, according to the present invention, there is provided a liquid chromatograph pump comprising a cylinder and a plunger reciprocating in the cylinder at a driving speed, the plunger being formed on its outer surface with a stepped part along the driving direction of the plunger so as to define a working chamber having a cross-sectional area between the stepped part and the inner wall surface of the cylinder, wherein the flow rate of the liquid chromatograph pump is determined by both cross-sectional area of the working chamber and driving speed of the plunger.

In view of the above-mentioned configuration, there may be provided a first pump incorporating a first cylinder, and a first plunger reciprocating in the first cylinder, and a second pump incorporating a second cylinder, and a second plunger reciprocating in the second cylinder, a suction valve being provided on the upstream side of the first pump, a discharge valve being provided on the downstream side of the first pump, and the stepped part being formed at least on the outer peripheral surface of the second plunger in the second pump, along the driving direction of the second plunger so as to define the working chamber between the stepped part and the inner wall surface of the second cylinder, wherein the second pump is located at the most downstream position among a plurality of pumps provided in the liquid chromatograph pump.

Further, there may be provided a first pump incorporating a first cylinder, and a first plunger reciprocating in the first cylinder, and a second pump incorporating a second cylinder, and a second plunger reciprocating in the second cylinder, a suction valve being provided on the upstream side of the first pump, a discharge valve being provided on the downstream side of the first pump, and the stepped part being formed at least on the outer peripheral surface of the second plunger in the second pump, along the driving direction of the second plunger so as to define the working chamber between the stepped part and the inner wall surface of the second cylinder, wherein the working chamber of the second pump is connected thereto with a discharge passage from the liquid chromatograph pump, a working chamber defined in the first pump is connected thereto with a suction passage connected to the liquid chromatograph pump, and the first pump and the second pump are preferably connected with each other in series.

Further, in order to achieve the first object, according to the present invention, there is provided a liquid chromatograph pump comprising a cylinder having an inner wall surface, and a plunger reciprocating in the cylinder at a driving speed, the plunger being formed on its outer surface with a stepped part along the driving direction of the plunger so as to define a working chamber between the stepped part and the inner wall surface of the cylinder, wherein an end part of the plunger on the side remote from the drive side, is exposed to a gas atmosphere.

In view of the above-mentioned configuration, there may be provided a first pump incorporating a first cylinder, and a first plunger reciprocating in the first cylinder, and a second pump incorporating a second cylinder, and a second plunger reciprocating in the second cylinder, a suction valve being provided on the upstream side of the first pump, a discharge valve being provided on the downstream side of the first pump, and the stepped part being formed at least on the outer peripheral surface of the second plunger in the second pump, along the driving direction of the second plunger so as to define the working chamber between the stepped part and the inner wall surface of the second cylinder, wherein one end part of the second plunger on the side remote from the drive side is exposed to a gas atmosphere, and the second pump is located at the most downstream position among a plurality of pumps provided in the liquid chromatograph pump.

Further, there may be provided a first pump incorporating a first cylinder, and a first plunger reciprocating in the first cylinder, and a second pump incorporating a second cylinder, and a second plunger reciprocating in the second cylinder, a suction valve being provided on the upstream side of the first pump, a discharge valve being provided on the downstream side of the first pump, and the stepped part being formed at least on the outer peripheral surface of the second plunger in the second pump, along the driving direction of the second plunger so as to define the working chamber between the stepped part and the inner wall surface of the second cylinder, wherein one end part of the second plunger on the side remote from the drive side is exposed to a gas atmosphere, the working chamber in the second pump is connected thereto with a discharge passage from the liquid chromatograph pump, and a working chamber defined in the first pump is connected thereto with a suction passage connected to the liquid chromatograph pump, and the first pump and the second pump are connected to each other in series.

In the liquid chromatograph pump as stated above, an eluent reserving container for reserving eluent to be fed by the liquid chromatograph pump is provided, a low pressure pump is provided between the eluent reserving container and the first pump, and a change-over valve, a passage communicated to the eluent reserving container and a passage communicated to a column are provided on the downstream side of the second pump, wherein the low pressure pump is operated so as to feed liquid at a large flow rate so as to fill the eluent in the passages on the downstream side while discharging air bubbles remaining in the pumps and the passages, thereafter, the change-over valve is connected to the passage communicated to the column, and then a trace of the eluent is fed by the first pump and the second pump.

Further, in order to achieve the second object, according to the present invention, there is provided a liquid chromatograph pump system comprising a liquid chromatograph pump, a container for reserving a solution, a low pressure pump provided between the liquid chromatograph pump and the container, a first passage for returning eluent discharged from the liquid chromatgraph pump into the container, a second passage for feeding the eluent discharged from the liquid chromatograph pump, and a change-over valve for changing over communication between the first passage and the second passage.

The liquid chromatograph pump is most effective in a liquid flow rate range from about 0.1 nL/min to 50 µL/min.

Further objects and advantages of the present invention will be apparent from the following description of preferred embodiments of the present invention which will be explained with reference to accompanying drawings wherein:

DETAILED DESCRIPTION OF THE INVENTION

Explanation will be made of an embodiment of the present invention with reference to the accompanying drawing.

Figure 1:
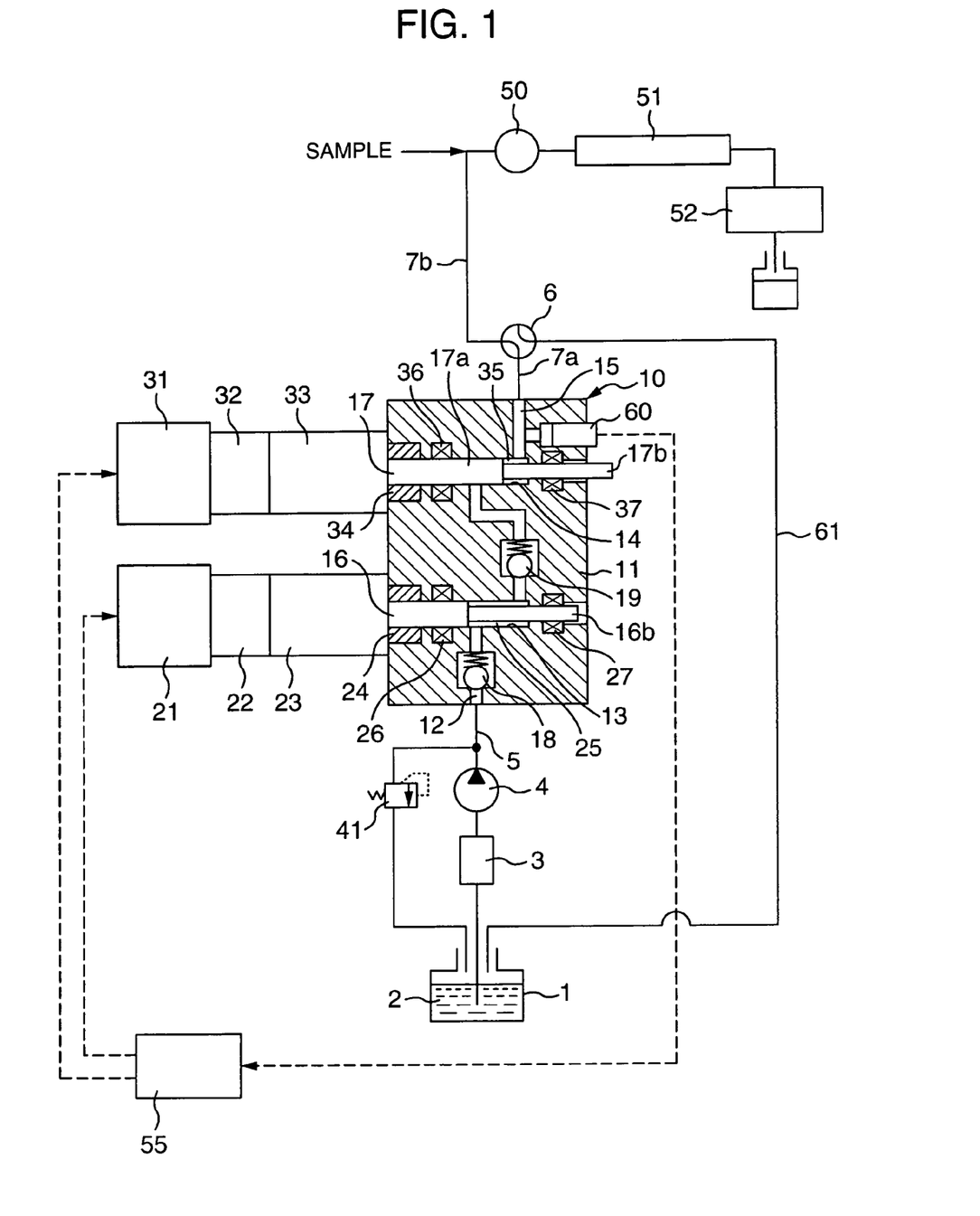
FIG. 1 is a schematic view illustrating a configuration of a hydraulic circuit in a liquid feed system in which a liquid chromatograph pump according to the present invention is applied.
Figure 2:
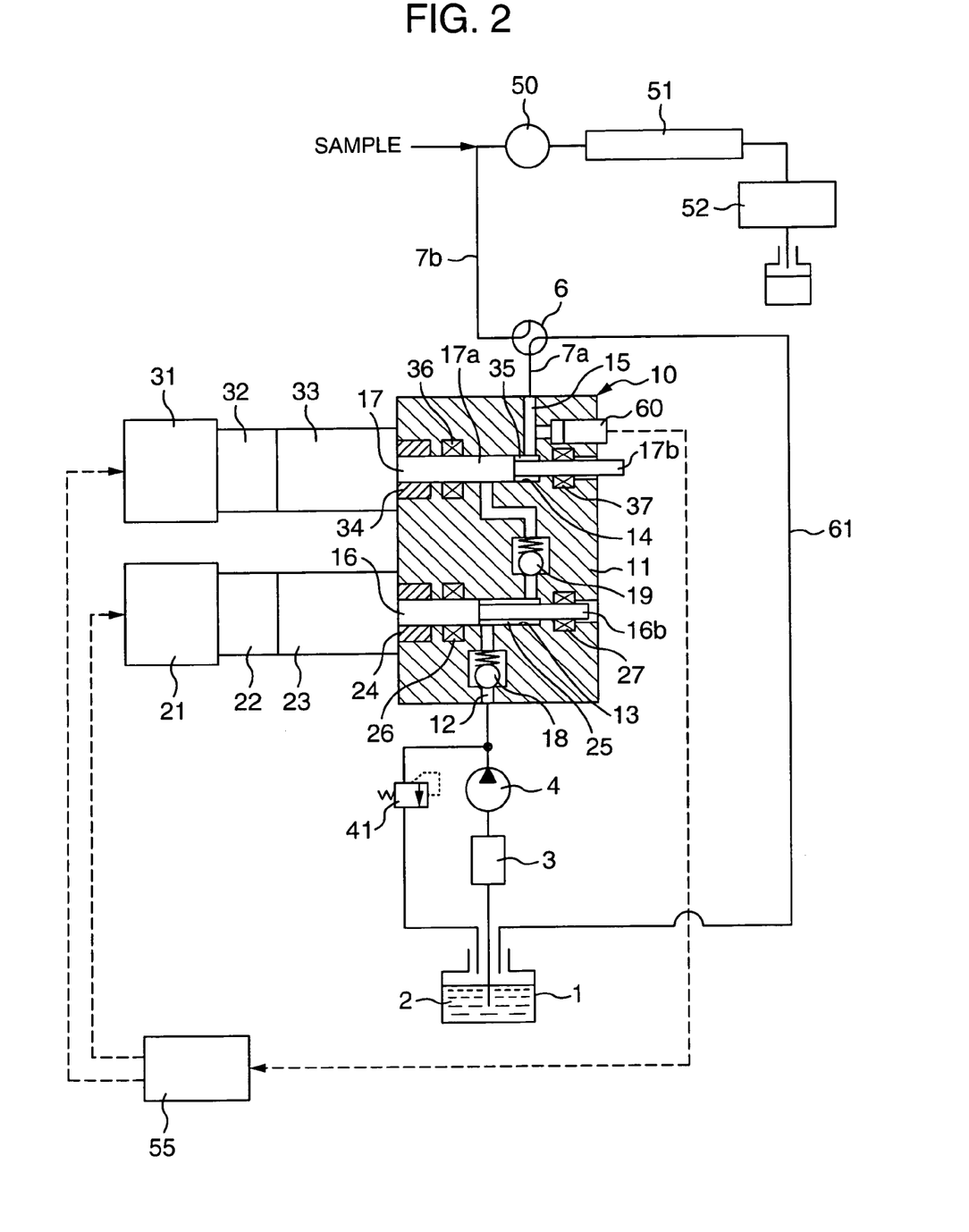
FIG. 2 is a schematic view illustrating the configuration of the hydraulic circuit in a liquid feed system in which a liquid chromatograph pump according to the present invention is applied.
Figure 3A:
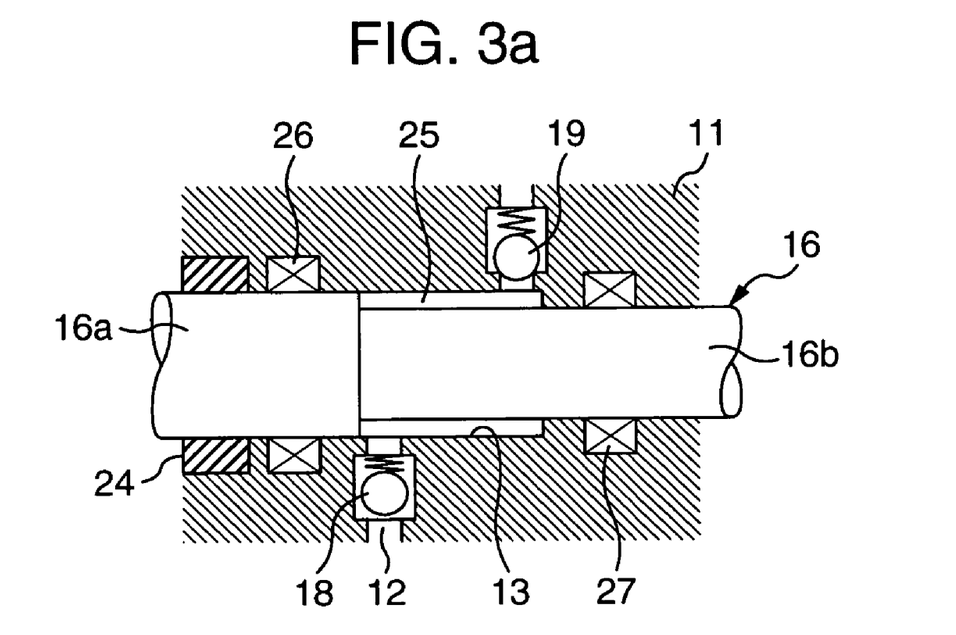
FIGS. 3a and 3b are enlarged sectional views schematically illustrating the configuration of the body of the liquid chromatograph pump according to the present invention.
Figure 3B:
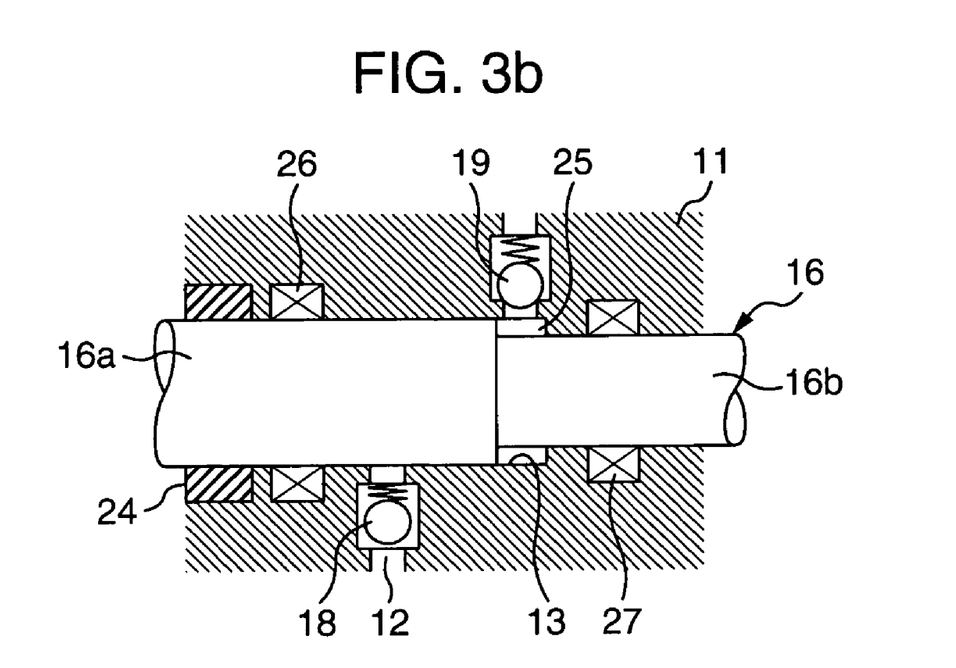
Figure 4:
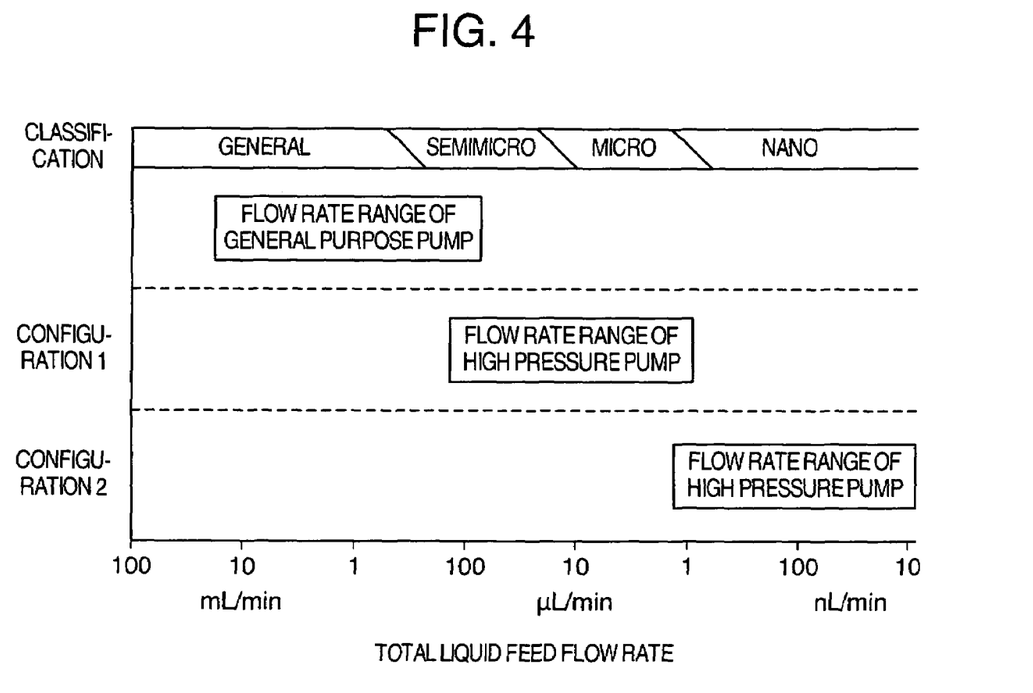
FIG. 4 is a view for flow rate ranges of various pumps including the liquid chromatograph pump according the present invention.
Figure 5:
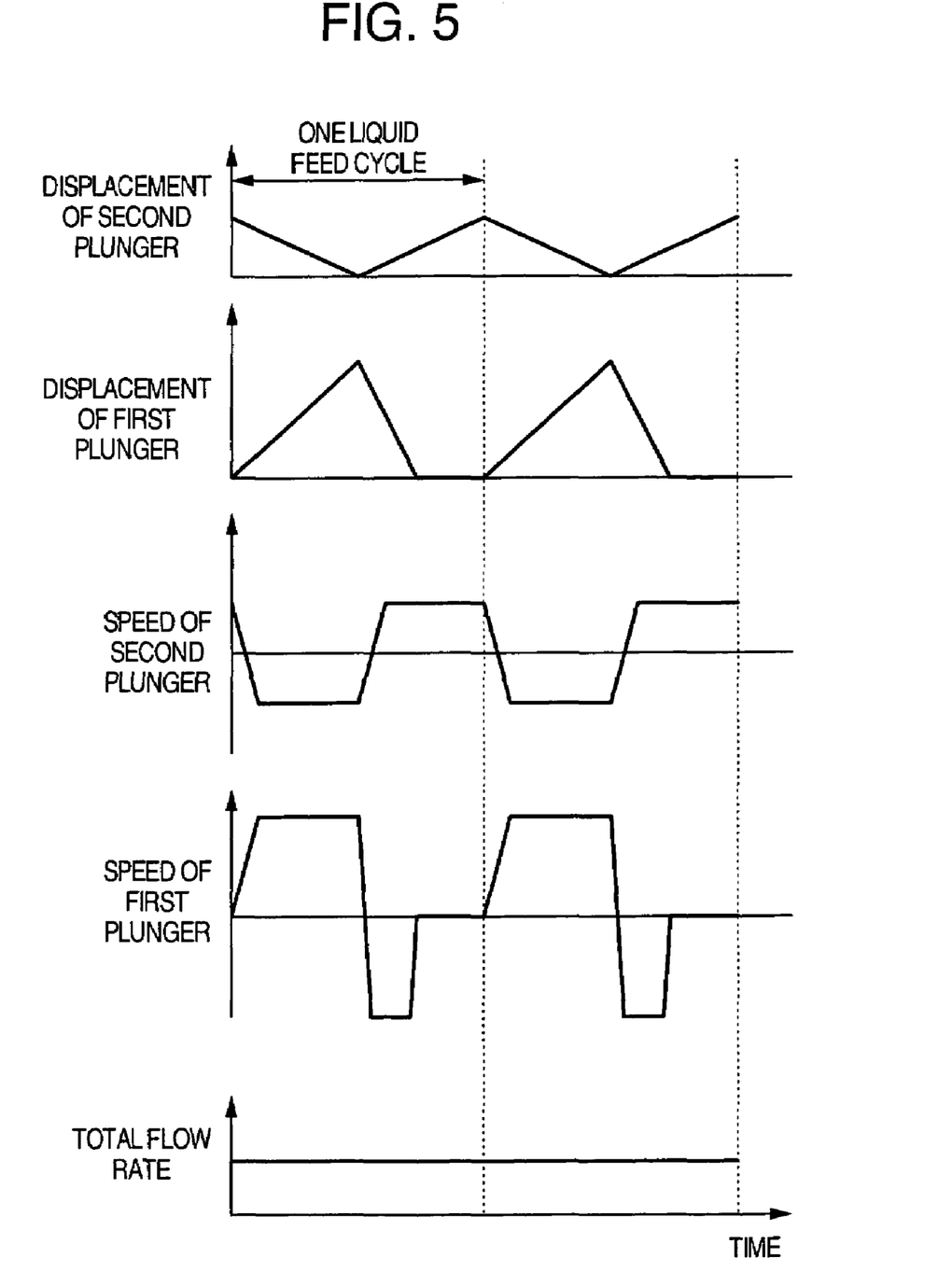
FIG. 5 is a view illustrating an example of a method of driving the liquid chromatograph pump according to the present invention.

FIG. 1 and FIG. 2 are views illustrating a schematic configuration of a hydraulic circuit in a liquid feed system for liquid chromatograph, in which a liquid chromatograph pump is used, FIG. 3 is an enlarged sectional view illustrating a schematic configuration of a bump body of the liquid chromatograph pump, FIG. 4 is a view illustrating flow rate ranges of pumps, and FIG. 5 is a view illustrating an example of a method of driving the liquid chromatograph pump.

Referring to FIGS. 1 to 3, the liquid feed system includes a liquid chromatograph pump for sucking eluent 2 from an eluent reserving or holding container 1 by way of a degasser 3, a low pressure pump 4 and an suction pipe line 5, an injector 50 receiving the eluent discharged from the liquid chromatograph pump, for injecting a sample to be analyzed by way of a change-over valve 6 and discharge pipe lines 7a, 7b, a column 51 charged therein with silica gel micro particles, a detector 52 for analyzing each of eluted components, a controller 55 for delivering drive signals to motors 21, 31 for driving the pumps, a pressure sensor 60 provided in the liquid chromatograph pump 10 for detecting a pressure, and delivering a detection signal thereof to the controller 55, a pressure control valve 41 for regulating a discharge pressure of the low pressure pump 4, a bypass pipe line 61 communicating the discharge pipe line 7a to the eluent reserving container 1 by way of the change-over valve 6.

The liquid chromatograph pump 10 is composed of a pump body 11, the motors 21, 31, speed reducing mechanisms 22, 32 and rectilinear drive mechanisms 23, 33.

The pump body 11 is formed therein with a suction passage 12, a first cylinder 13, a second cylinder 14 and a discharge passage 15, and a first plunger 16 and a second plunger 17 are slidably accommodated in the first cylinder 13 and the second cylinder 14, being held by means of bearings 24, 34, respectively. An intake valve 18 is incorporated in the intake passage 12, and a discharge valve 19 is incorporated in an intermediate passage communicating between the first cylinder 13 and the second cylinder 14. These valves are urged in one direction by means of springs, respectively, so as to constitute check valves for limiting the flowing direction of the eluent. That is, the spring urges the intake valve 18 and the discharge valve 19 so that the intake valve 18 is opened overcoming its associated spring when the first pump carries out its intake stroke, and the discharge valve is opened overcoming its associated spring when the first pump carries out its discharge stroke.

The speed of the motor 21 is reduced by the speed reducing mechanism 22, and the rotational motion thereof is converted into a rectilinear motion by a rectilinear drive mechanism in order to reciprocate the first plunger 16 in the first cylinder 13. Similarly, the second plunger 17 is reciprocated in the second cylinder 14 by an actuator composed of the motor 31, the speed reducing mechanism 32 and the rectilinear drive mechanism 33.

As shown in FIGS. 3a and 3b in detail, the first plunger 16 is formed in a stepped part, that is, it is composed of a large diameter part 16a on the motor side and a small diameter part 16b on the side remote from the motor. A first working chamber 25 is defined between the first stepped part and the inner wall surface of the first cylinder 13. That is, the first working chamber 25 is defined by the shoulder surface by which the large diameter part 16a and the small diameter part 16b abut each other, and the outer peripheral surface of the small diameter part 16b of the first plunger 16, and an end surface part of the first cylinder 13 through which a through-bore for allowing the small-diameter part 16b to pass therethrough is formed. Seals 26, 27 prevent leakage of liquid from the large diameter part 16a and the small diameter part 16b of the plunger 16, respectively.

Similarly, the second plunger 17 is formed therein with a stepped part, that is, it is formed of a large diameter part 17a and a small diameter part 17b, and a second working chamber 35 is defined between the stepped part and the inner wall surface of the second cylinder 14. Seals 36, 37 effect oil-tightness for the large diameter part 17a and the small diameter part 17b.

As the working chambers 16, 17 are defined between the stepper parts formed on the outer peripheral surfaces of the plungers 16, 17 and the cylinders 13 and 14, respectively, it is possible to facilitate decreasing of the cross-sectional areas of the working chambers in a plane transverse to the drive directions of the plungers 16, 17, and accordingly, a trace of liquid can be fed while the drive values of the plungers 16, 17 are set to be large more or less. Further, it is conceivable that in order to further promote the feed of a trace of liquid, the formation of such a stepped part in a small-sized and precise manner is relatively simpler than enhancement of the accuracy of rotation of the motors and the accuracy of travel of the plungers 16, 17.

The front end parts of small diameter parts of the plungers 16, 17 are exposed to a gas atmosphere (the atmosphere in this embodiment). This fact is greatly different from the conventional technology as stated above, in which the small diameter part of a different diameter plunger is present within an eluent liquid environment (liquid passage). That is, the front end parts of the small diameter parts 16b, 17b are located outside of the working chambers 25, 35, and are not present any other working chambers. In the liquid chromatograph pump 10 in this embodiment, only the stepped parts formed on the plungers 16, 17 define working chambers in the pumps together with the associated cylinders, allowing the front end parts of the small diameter parts 16, 17 to be ineffective for pumping work.

Further, the exposition of the front end parts of the small diameter parts 16b, 16b to the gas atmosphere is convenient for removal of deposits such as organic solvent sticking to the seal (for example, salt which is crystallized into a powder form and sticks to the seals when an aqueous solution containing salt is fed).

In this embodiment which will be detailed, hereinbelow, the portion including the first plunger 16 and the actuator for driving the first plunger 16 will be referred to as "first pump", and the portion including the second plunger 17 and the actuator for driving the second plunger 17 will be referred to as "second pump".

Next, referring to FIG. 4 for explaining flow rate ranges of liquid chromatograph pumps (which will be hereinbelow referred to as "high pressure pumps") and the classification thereof, in this embodiment, there will be explained a liquid chromatograph pump for feeding liquid at an extremely low flow rate below a semi-micro flow rate, that is, a micro flow rate (μl) or a nano-flow rate (nl). As understood from an example of a flow rate range of a general purpose pump as shown in FIG. 4, the ratio between a maximum flow rate and a minimum flow rate cannot in general exceed about 100 due to constraints as to a motor speed range, accuracy of rotation and the like. Thus, should the flow rate be set in a micro or nano range, the maximum flow rate would be automatically less. Thus, there are presented serious problems, that is, it takes a long time to charge eluent into passages in a measuring system downstream of the pump during a start of a test, and air bubbles stagnating in the pump cannot be easily discharged. In particular, should air bubbles remain in the cylinder, the reciprocation of the plunger would mainly cause compression and expansion of only air bubbles so that the liquid is not discharged substantially. If air bubbles are present in the cylinder, the air bubbles are merely compressed and expanded, and accordingly, the liquid not discharged, or the quantity thereof is extremely small. Thus, there would be caused such a problem that no measurements with a high degree of accuracy can be made.

Accordingly, in the configuration of the embodiment of the present invention, the liquid feed at an extremely low flow rate is carried out by the high pressure pumps, but the charge of eluent and discharge of air-bubbles are carried out by a low pressure pump upon a start of a test.

Referring to in FIG. 4, as understood from examples 1, 2, the flow rate range of the high pressure pumps are set to cover a micro or nano flow rate range. On the contary as to the low pressure pump, it is sufficient to set the flow rate range of the low pressure pump so as to charge eluent and discharge air bubbles upon a start of a test within a short time, as stated above, although it is not absolutely required to set the flow rate range of the lower pressure pump It is noted here that the total feed flow rate taken along the abscissa in FIG. 4, exhibits a total feed flow rate of liquid to be fed during high pressure gradient operation which will be explained later. Since the gradient operation changes the flow rate through steps of several tenths or several hundreds, the minimum flow rate which can be discharged by the high pressure pump becomes lower by single or double figures.

Explanation will be hereinbelow made of the specification of the plunge diameter of the high pressure pump with such an assumption that the gradient operation is carried out through 100 steps. It is noted that since the flow rate is determined by the cross-sectional area of the plunger and the speed, the flow rate can be changed by changing the diameter of the plunger or the speed of the motor or the speed reduction rate.

The diameter of the large diameter part of the plunger shown in FIG. 3 is denoted by D, and that of the small diameter part thereof is denoted by d while the speed reduction ratio is estimated as 1/10 or 1/20 in comparison with general-purpose pumps. In the case of the example 1, if D=2 mm, there would be d=about 1.5 mm. Meanwhile, in the case of the example 2, there would be d=1.99 to 1.98 mm.

With this configuration, explanation will be made of a method of operating the liquid chromatograph pump with reference to FIGS. 1, 2 and 5. It is noted that FIG. 5 shows a displacement of a second plunger pump 17, a displacement of the first plunger 16, a speed of a second plunger 17, a speed of the first plunger 16 and a total flow rate flowing through the discharge passage 11, which are indicated in the mentioned order as viewed from the top, with respect to a time taken along the abscissa.

At first, when the solution is charged in the pump while air bubbles are discharged therefrom at a preparation stage for a test, the change-over valve 6 is changed over onto the bypass pipe line 61 side, as shown in FIG. 2, so as to communicate the discharge pipe line 7a of the high pressure pump 10 with the bypass pipe line 61, and then the low pressure pump 4 is started. When the low pressure pump 4 is operated, the eluent 2 is sucked from the eluent reserving container 1 while air bubbles solved in the eluent are removed by the degasser 3. It is noted here that since the pressure regulating valve 41 for regulating the discharge pressure of the low pressure pump 4 is incorporated on the discharge side of the low pressure pump 4 so as to normally regulate the discharge pressure at a value not greater than 0.5 to 0.6 MPa. This value can be adjusted. The eluent discharged is retuned into the eluent reserving container 1 by way of the intake passage 12, the intake valve 18, the first working chamber 25, the discharge valve 19, an intermediate passage, and a working chamber 35, the discharge passage 15, and a discharge pipe line 7a, the change-over valve 16 and the bypass pipe line 61.

With the provision of the low pressure pump 4 which feeds a liquid at a high flow rate, air bubbles stagnating in the downstream side high pressure pump 10 can be simply discharged. In particular, in the high pressure pump 10 in this embodiment, with the provision of such a configuration that the solution is introduced from the working chambers 25, 36 in the vicinity of the bottom dead centers thereof while the solution is discharged therefrom in the vicinity of the top dead centers thereof, no stagnation occurs in the working chambers 25, 35, and accordingly, air bubbles can be prevented from stagnating therein. With this configuration, the preparation for a test can be completed within a period which is equal to or shorter than that can be made by general-purpose liquid chromatograph pumps. It is noted that there would be caused no problems even though the high pressure pump 10 is either rested or operated in this period.

Next, when the operation is shifted into a steady-state operation, the change-over valve 6 is changed over into the discharge pipe line 7b side, as shown in FIG. 1, so as to communicate the discharge pipe line 7a of the high pressure pump 10 with the discharge pipe line 7b so as to establish a liquid feed line connected to the detector 52.

Although the low pressure pump 4 is operated, the liquid feed at a low flow rate is carried out by the high pressure pump 10. The eluent 2 is sucked into the pump by way of the intake passage 12, and is discharged from the discharge passage 15. Thereafter, it is led through the change-over valve 6 and the discharge pipe lines 7a, 7b and into the injector 53 which injects a sample to be analyzed. The mixed solution is led into the column 51 so as to be isolated into a plurality of components which are analyzed respectively by the detector 52. Since silica gel micro-particles are charged in the column 51, a load pressure of about 10 MPa is effected in the high pressure pump by a flow resistance caused by the solution passing thereghrough. The degree of this pressure varies, depending upon the diameter of the column 51 and the and the flow rate of the solution passing thereghrough.

FIG. 5 shows an example of a drive pattern of the high pressure pump 10. Since the flow rate is in proportion to the speed of the plunger, the velocity wave-form is equaivalent to the flow rate waveform.

In order to make the sum of the speeds of the first plunger 16 and the second plunger 16 become always constnat, that is, the total flow rate is always constant, the drive of the first plunger 16 and the second plunger 17 is controlled. In this embodiment, the first pump and the second pump are configured in one and the same specification. That is, the first plunger 16 and the first working chamber 25 have the same shape and the same dimensions as those of the second plunger 17 and the second working chamber 35. Further, when the second chamber 17 carries out a discharge stroke, the discharge valve 19 (which serves as a suction valve as viewed from the second pump side) is closed, and accordingly, the solution is fed from the discharge passage 15 at a flow rate which is determined by the drive speed of the second plunger 17 and the cross-sectional area of the second working chamber 35. At this time, the first plunger 16 carries out a suction stroke while the suction valve 18 is opened. When the second plunger 17 carries out a suction stroke while the first plunger 16 carries out a discharge stroke, the suction valve 18 is closed but the discharge valve 19 is opened. Since the first plunger 16 is driven at a speed which is two times as high as the speed of the second plunger 17. Thus, the second pump 2 is replenished while the solution is discharged at a flow rate which is substantially equal to that discharged by the first pump during the discharge stroke.

Thus, in this embodiment, in addition to the operation during the discharge stroke of the second pump, even during the intake stroke of the second pump, the liquid feed is carried out at a flow rate which is equal to that discharged by the second pump during the discharge stroke. Accordingly, pulsation caused in the flow rate discharged from the liquid chromatograph pump 10 is reduced, thereby it is possible to stably feed the liquid with less pulsation.

In the method of operating the liquid chromatograph pump as stated above, the discharge quantity of the first pump having the first plunger 16 is larger than that of the second pump having the second plunger 17, and accordingly, it is conceivable that the cross-sectional area of the working chamber of the first pump may not be decreased to that of the working chamber of the second pump. In this case, the working chamber of the first pump may be defined by the front end part of the first plunger 16, instead of the stepped part thereof. However, as in the configuration of this embodiment, if no appreciable difference in flow rate is present among a plurality of pumps, or if the flow rate is less, it is preferable to define the working chambers 25, 25 of the plurality of pumps by the stepped parts formed on the plungers 16, 17. Thereby it is possible to surely feed a trace of liquid and to stabilize the liquid feed.

Anyway, in order to feed a trace of liquid from the liquid chromatograph pump 10, of a plurality of pumps provided in the liquid chromatograph pump 10, the working chamber 35 of the one which is located nearest to the discharge passage 15 (that is, the working chamber 35 is connected to the inlet of the discharge passage 15), is defined by the stepped part of the plunger 17, and the front end part of the small diameter part 17b of the plunger 17 is exposed to the gas atmosphere. Alternatively, the flow rate of liquid discharged from liquid chromatograph pump 10 is determined by the cross-sectional area or volume of the second pump or the working chamber defined by the stepped part of the plunger 17.

Figure 6:
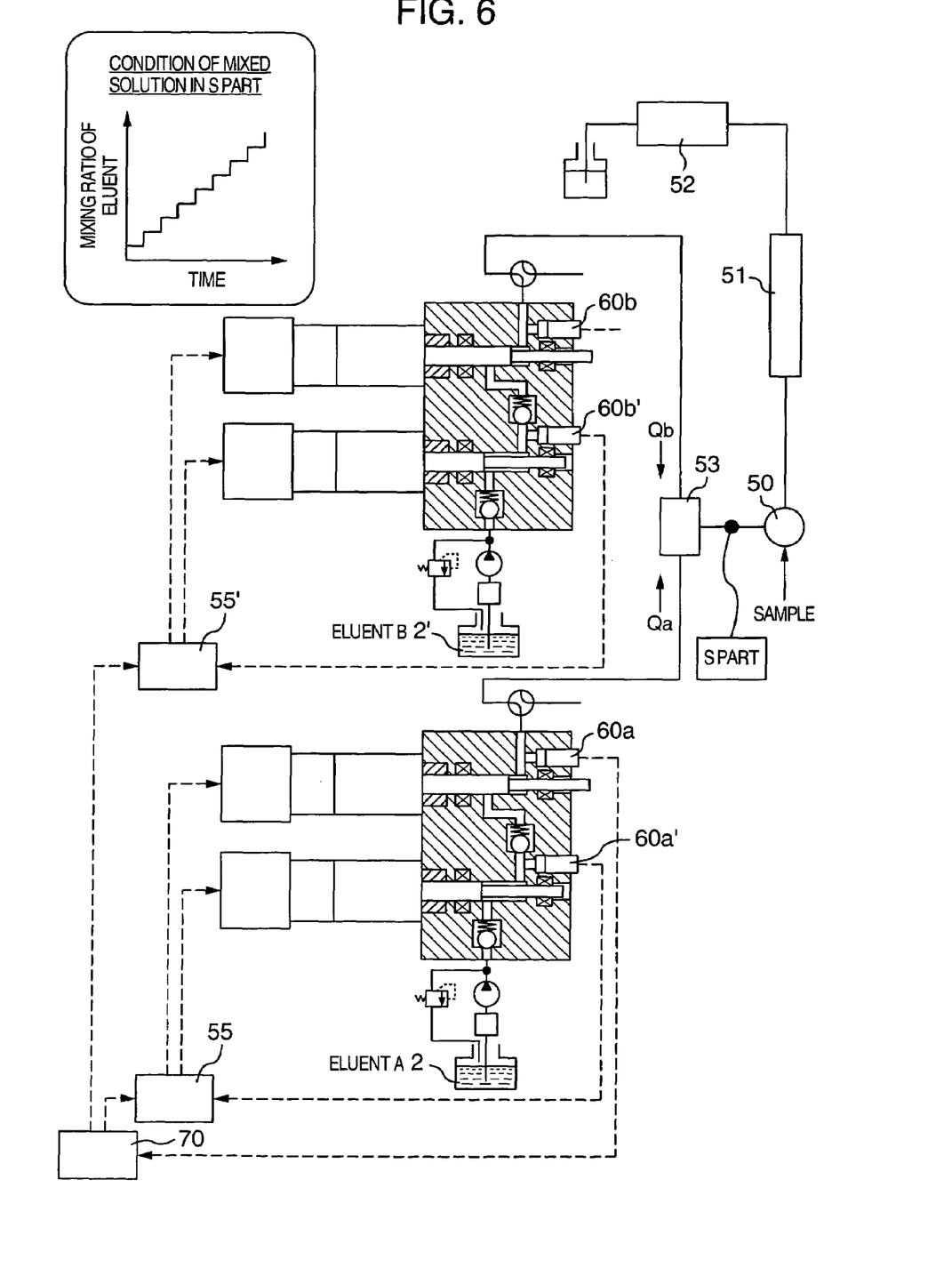
FIG. 6 is a view illustrating an example of a configuration of a system in which the liquid chromatograph pump according to the present invention is applied.

Next, FIG. 6 shows an example in which two liquid feed system according to the present invention are used to constitute a high pressure gradient system. The so-called gradient operation is carried out in such a way that the mixing ratio of two kinds of eluents A, B is stepwise changed with time, that is, the rate of Qa and Qb is changed while the total liquid feed quantity (=Qa+Qb) is maintained to be constant during a test.

Figure 7:
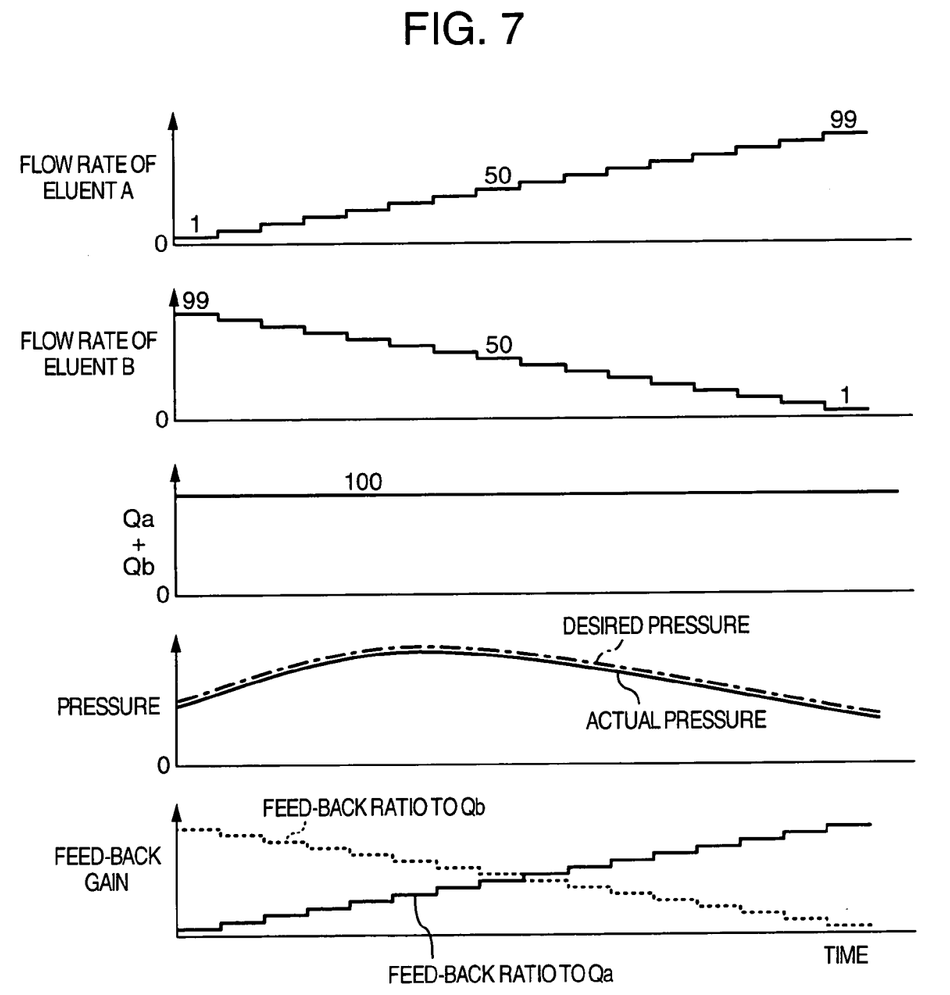
FIG. 7 is a view illustrating an example of a method of driving the liquid chromatograph pump according to the present invention.

Referring to FIG. 7 which shows time variation of several parts in the gradient operation, while maintaining Qa+QB constant at 100, the ratio is changed from Qa:Qb=1:99, to 2:98, 3:97, . . . 50:50, . . . 99:1, successively. This gradient has 100 stages, and accordingly, with 1 μL/min of a total liquid feed flow rate, it is required to 10 nL/min which is 1/100 of the total liquid feed flow rate, for the minimum flow rate and the resolution. It has been known that even though the liquid is fed at a constant flow rate, the flow resistance of the liquid passing through the column is changed due to composition change in the mixture, and accordingly, the discharge pressure of a pump is changed by about 1.5 to 2 times at maximum. Thus, should the pressure be maintained to be constant, the flow rate would vary.

Meanwhile, the relationship between the mixing ratio and the pressure variation has previously been known from paste experimental data, and accordingly, a curve of pressure variation is predictable whn the flow rate is constant. Thus, with using a theoretical value from the curve of pressure variation as a desired value, the pump is driven through feed-back control in accordance with a pressure sensor signal so as to adjust an actual pressure to the desired pressure, and accordingly, the liquid can be fed at a constant total liquid flow rate with a high degree of accuracy. Specifically, a signal from the pressure sensor 60a is fed back to the main controller 70 so as to control controllers 55, 55' for the pumps in order to allow the pressure to follow the desired pressure. It is noted that the discharge passage from both pumps are communicated with each other through the intermediary of a mixer 53, and accordingly, the pressure is substantially constant among various parts, thereby it is possible to use a signal from either one of the pressure sensors 60a, 60b.

At this time, if the actual pressure is lower than the desired pressure, it indicates that the total liquid feed flow rate (Qa+Qb) is lower, and accordingly, the speeds of the motors are increased to increase the flow rate. However, it cannot be determined that either Qa or Qb is low. In such a case that Qa is actually lower, the correction should be made with erroneous determination of lowering of Qb, the accuracy of the mixing ratio would be deteriorated. It is a problem of the so-called correlative interference during the gradient operation.

In order to avoid occurrence of the above-mentioned problem, in this embodiment, the connection is made with such an assumption that both Qa and Qb are lowered at an equal rate. This can be carried out by applying a feed-back gain which is proportional to a flow rate ratio as shown. For example, in the case of the operation with the flow rate Qa:Qb=20:80, the feed back gains for Qa, Qb are given by (20/100)×K and (80/100)×K, respectively, where K is a constant. If the total liquid feed rate is insufficient, proportional control is carried out with instruction values of Qa and Qb, which are given by 30+(20/100)×K×50 and (80/100)×K×50, respectively. For example, if K=1, the former becomes 21, and the later becomes 84. In this way, the problem of correlative interference can be avoided although it is impossible to prevent the mixing accuracy from lowering due to individual difference between two pumps, thereby it is possible to prevent the accuracy of mixing from further lowering.

It is noted that since the discharge pressure varies with time, the pressures in the first working chambers of both pumps should be changed correspondingly. In particular, in the case of lowering the pressure in the pressure sensor 60a, 60b parts, the discharge valve is opened so that eluent flows from the first working chamber into the second working chamber, and accordingly, the liquid feed quantity is increased. In view of this fact, in this embodiment, pressure sensors 60a, 60b are provided in the first working chambers of the both pumps, respectively, and signals therefrom are fed back to the controllers 55, 55' which therefore control in such a way that the first plunger is driven to set the pressure in the first working chambers to be equal to a discharge pressure measured by the pressure sensor 60a.

In view of the foregoing, it is possible to provide a high pressure gradient system which is excellent in liquid feed stability and mixing accuracy.

Figure 8:
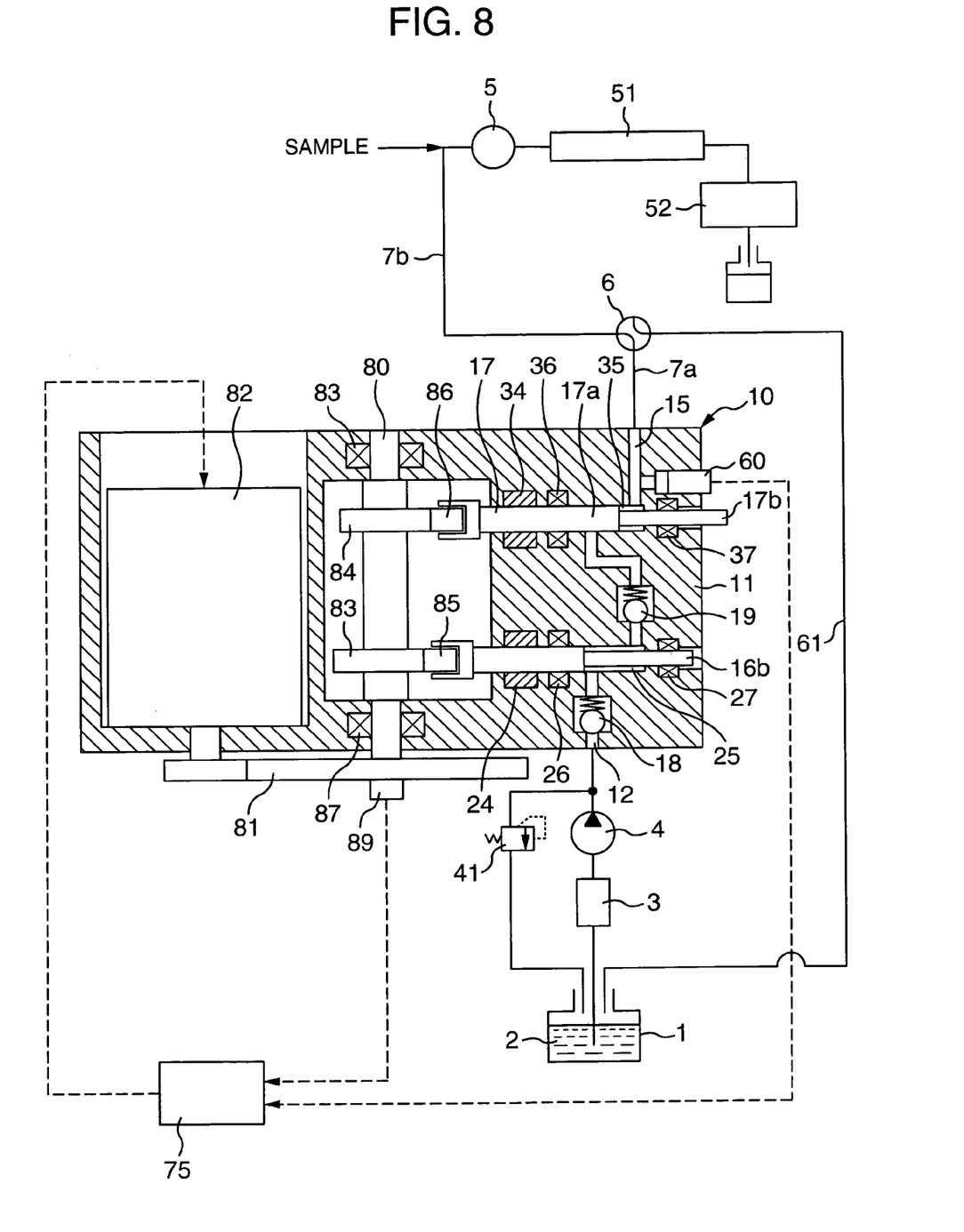
FIG. 8 is a schematic view illustrating a configuration of another hydraulic circuit in which the liquid chromatograph pump according to the present invention is applied.

Although explanation has been hereinabove made of an example of the liquid feed system in which the liquid chromatograph pump according to the present invention is applied as a direct drive type, the present invention should be limited to this configuration. That is, the liquid chromatograph pump may be driven by cams actuated by motors. Referring to FIG. 8 which shows a hydraulic circuit as an example of a schematic configuration of another liquid feed system, like reference numerals are use to denote like parts to those in the embodiment stated above in order to abbreviate the explanation thereto.

The liquid feed system shown in FIG. 8, there are provided a cam shaft 80 of a liquid chromatograph pump, a motor 82 coupled to the cam shaft 80 through the intermediary of a speed reducer 81, for rotating the cam shaft 80, a first cam 83 and a second cam 84 integrally incorporated with the cam shaft 80, a first roller follower 85 and a second roller follower 86 which carry out rotation and slide in cooperation with these cams, bearings 87, 88 for rotatably journaling the cam shaft 80, an angular sensor 89 provided on the cam shaft 80, for detecting a rotating angle of the cam, and a controller 75 for delivering a control signal to the motor 82.

The controller 75 receives detection signals from the pressure sensor 60 provided in the pump 10, the angular sensor 89 and the like, and carries out a predetermined computation from the detection signals so as to deliver the thus created drive instruction signal to the motor 82.

Figure 9:
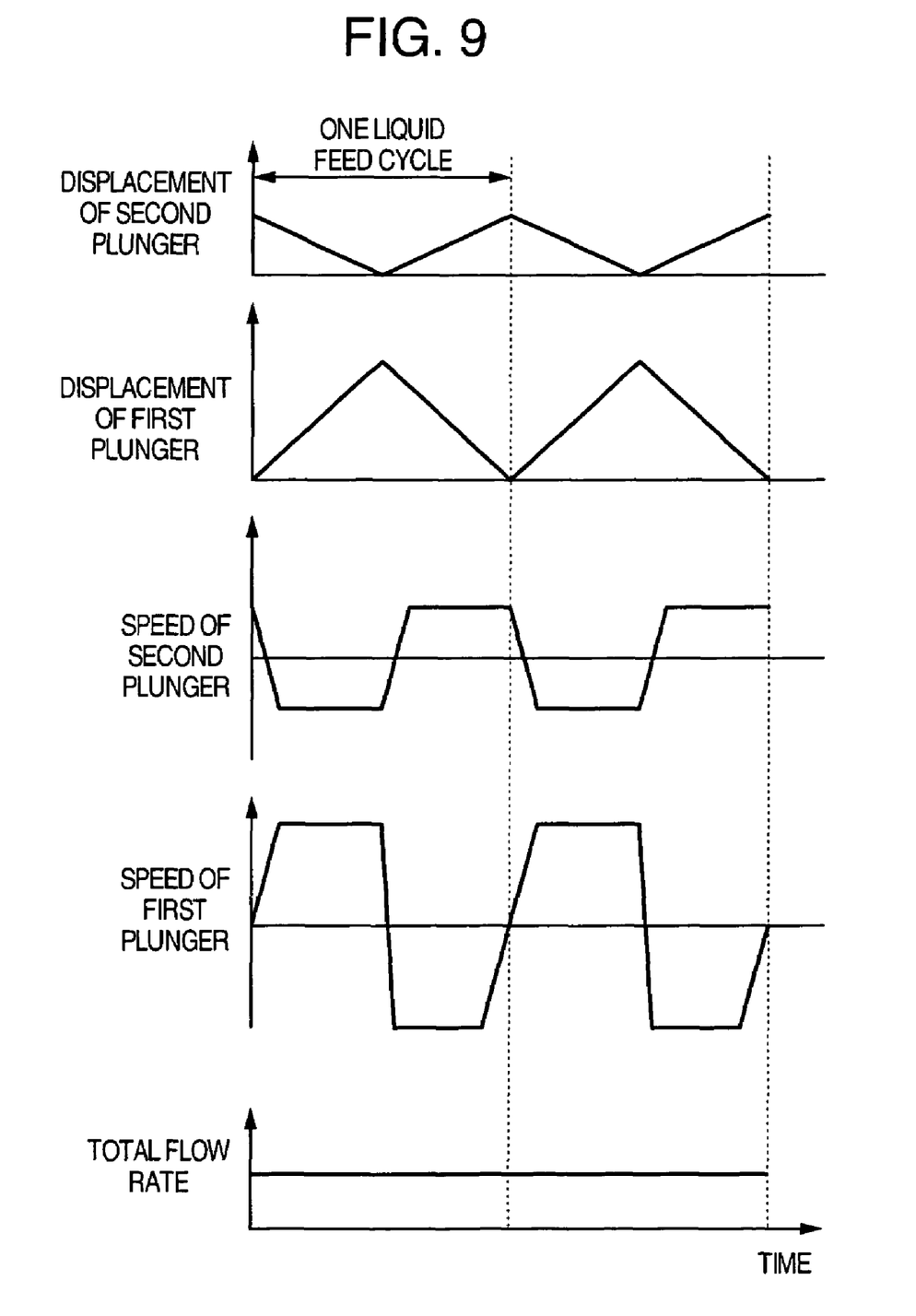
FIG. 9 is a view illustrating an example of a method of driving the liquid chromatograph pump according to the present invention.

With the above-mentioned configuration, explanation will be made of a method of operating the liquid chromatograph pump in this embodiment with reference to FIGS. 8 and 9. It is noted that FIG. 9 shows a displacement of the second plunger 17, a displacement of the first plunger 16, a speed of the second plunger 17, a speed of the first plunger 16 and a total flow rate flowing through the discharge passage 11 in the mentioned order as view from the top.

At the stage before a test, such an operation mode that air bubbles are expelled from the inside of the pump, and eluent is filled in the pump is carried out in the same manner as that stated above, and accordingly, the details of this operation mode will be abbreviated. Explanation will be made of a steady state operation.

The change-over valve 6 is switched to the discharge pipe line 7b side so as to communicate the discharge pipe line 7a of the high pressure pump 10 with the discharge pipe line 7b so as to establish a liquid feed line connected to the detector 52. Then, control is made in such a way that the sum of the speed of the first plunger 16 and the second plunger 17 is always set to a constant value, that is, in order to maintain the total flow rate at a constant value. Specifically, the speed of the first plunger 16 is two times as high as that of the second plunger, and the second pump is replenished with the liquid while the liquid is discharged therefrom. Thus, during intake stroke of the first pump. The intake valve is operated, and accordingly, only the second pump feeds the liquid.

With the configuration as stated above, the liquid chromatograph pump can be constituted by a single motor, and accordingly, it is possible to make the liquid feed system compact.

It is noted that an extremely low flow rate as mentioned above can be obtained by a piezoelectric actuator, an actuator in which thermal expansion of metal is used so as to control a displacement by thermal control thereof, or the like, instead of the motor and the direct drive mechanism or the motor and the cam drive mechanism.

Next, explanation will be made of a method of controlling the displacement with the use of the thermal expansion of the metal under thermal control. With setting the minimum flow rate of the pump to 0.1 nL/min (which is the discharge quantity of the pump in the case of 100 stages of gradient in the configuration 2 shown in FIG. 4), as the plunger diameter is $\phi 2$, the averaged feed speed of the plunger is $3.2 \times 10^{-5}$ mm/min. Meanwhile, the thermal expansion coefficient of iron is $1.0 \times 10^{-5}$/deg.C, and accordingly, the order of the feed speed of the plunger is the same as that of the thermal expansion coefficient of iron. Thus, by directly or indirectly controlling the temperature of the plunger with 1 deg.C/min, the plunger can be displaced so as to feed the above-mentioned discharge quantity of liquid. As a measure for carrying out the above-mentioned temperature control, there may be used a thermo-module (a semiconductor cryogenic thermal element which exhibit a temperature difference under current running), a refrigerating air-conditioner or the like.

With the above-mentioned configuration in which no mechanical element is used for displacing the plunger, there may be exhibited such an advantage that the reliability of the system can be enhanced, and the maintenance thereof can be facilitated.

Further, in this embodiment, explanation has bee made of such a configuration that the two working chambers which are formed in one and the same pump body, are connected to each other through the intermediary of passages, there may be constituted such a configuration that two separate pumps are connected to each other by pipe lines. This configuration can facilitate the disassembly of the pump, and accordingly, the maintenance thereof such as the replacement of seals can be carried out in a simple way. Further, there may be such an advantage that the layout ability of equipments can be enhanced.

Explanation has been made of the liquid chromatograph pump according to the present invention which is applied in the technical fields of medical equipments. However, it goes without saying that the present invention can be applied in various fields other than the afore-mentioned fields, such as the technical fields of food equipments, chemical fields or general industrial machines, whenever the pump is used for feeding a trace of liquid.

According to the present invention, since the flow rate of liquid to be fed can be determined by a pump which is constituted by a stepped part formed on a plunger, thereby it is possible to provide a liquid chromatograph suitable for feeding a trace of liquid.

Further, since a trace of liquid is fed by a high pressure pump while the charge of eluent and the expelling of air bubbles before a start of a test are carried out a low pressure pump, thereby it is possible to provide a liquid chromatograph pump which can completely charge eluent and expel air bubbles in a short time before a start of a test.

Although the explanation has been made of the preferred embodiments of the present invention, the present invention should not be limited to these preferred embodiments, but various modifications and improvements of the present invention can be made within the technical scope and concept of the present invention which are only defined by the appended claims.

The invention claimed is:

1. A liquid chromatograph pump comprising:
an upstream-side plunger pump as a first pump and a downstream-side plunger pump as a second pump, said first and second pumps being connected fluidly in series;
a first motor for driving a plunger of the first pump and a second motor for driving a plunger of the second pump whereby the plunger of the first pump and the plunger of the second pump may be driven at different speeds from each other;
a first check valve arranged at an upstream side with respect to the first pump to prevent a liquid from flowing from the first pump to the upstream side with respect to the first pump when the plunger of the first pump moves forward to pressurize the liquid in the first pump, and to allow the liquid to flow toward the first pump from the upstream side with respect to the first pump when the plunger of the first pump moves backward to take the liquid into the first pump;
a second check valve arranged between the first and second pumps to prevent the liquid from flowing from the second pump toward the first pump when the plunger of the first pump moves backward to take the liquid into the first pump and the plunger of the second pump moves forward to pressurize the liquid in the second pump, and to allow the liquid to flow from the first pump toward the second pump when the plunger of the second pump moves backward to take the liquid into the second pump and the plunger of the first pump moves forward to pressurize the liquid in the first pump to make a flow rate of the liquid discharged from the first pump greater than a flow rate of the liquid taken into the second pump; and
first and second cylinders and said first and second plungers to form said first and second pumps, and a stepped part being formed at least on an outer peripheral surface of the second plunger in the second pump, along a driving direction of the second plunger so as to define a working chamber between the stepped part and an inner wall surface of the second cylinder,
wherein one end part of the second plunger on a side remote from a drive side is exposed to a gas atmosphere.

2. A liquid chromatograph pump comprising:
an upstream-side plunger pump as a first pump and a downstream-side plunger pump as a second pump, said first and second pumps being connected fluidly in series;
a first motor for driving a plunger of the first pump and a second motor for driving a plunger of the second pump whereby the plunger of the first pump and the plunger of the second pump may be driven at different speeds from each other;
a first check valve arranged at an upstream side with respect to the first pump to prevent a liquid from flowing from the first pump to the upstream side with respect to the first pump when the plunger of the first pump moves forward to pressurize the liquid in the first pump, and to allow the liquid to flow toward the first pump from the upstream side with respect to the first pump when the plunger of the first pump moves backward to take the liquid into the first pump;

a second check valve arranged between the first and second pumps to prevent the liquid from flowing from the second pump toward the first pump when the plunger of the first pump moves backward to take the liquid into the first pump and the plunger of the second pump moves forward to pressurize the liquid in the second pump, and to allow the liquid to flow from the first pump toward the second pump when the plunger of the second pump moves backward to take the liquid into the second pump and the plunger of the first pump moves forward to pressurize the liquid in the first pump to make a flow rate of the liquid discharged from the first pump greater than a flow rate of the liquid taken into the second pump; and first and second cylinders and said first and second plungers to form said first and second pumps, and a stepped part being formed at least on an outer peripheral surface of the second plunger in the second pump, along a driving direction of the second plunger so as to define a working chamber between the stepped part and an inner wall surface of the second cylinder, wherein one end part of the second plunger on a side remote from a drive side is exposed to a gas atmosphere, the working chamber in the second pump is connected with a discharge passage from the liquid chromatograph pump, and a working chamber defined in the first pump is connected with a suction passage connected to the liquid chromatograph pump.

3. A liquid chromatograph pump as set forth in claim 1 or 2, further comprising:

an eluent holding container for holding eluent to be fed by the liquid chromatograph pump, a low pressure pump being provided between the eluent holding container and the first pump, a change-over valve, a passage communicated to the eluent holding container and a passage communicated to a column being provided on the downstream side of the second pump, wherein the low pressure pump is operated so as to feed liquid at a large flow rate in order to fill the eluent in the passages on the downstream side while discharging air bubbles remaining in the pumps and the passages, and thereafter, the change-over valve is connected to the passage communicated to the column, and then a trace of the eluent is fed by the first pump and the second pump.

4. A liquid chromatograph pump as set forth in claim 1, wherein a liquid flow rate range is from about 0.1 nL/min to 50 μL/min.

* * * * *